(12) United States Patent
Chen et al.

(10) Patent No.: US 12,258,865 B2
(45) Date of Patent: Mar. 25, 2025

(54) COAL AND GAS OUTBURST MONITORING DEVICE

(71) Applicant: Henan Polytechnic University, Jiaozuo (CN)

(72) Inventors: Xu Chen, Jiaozuo (CN); Hongtu Zhang, Jiaozuo (CN); Zhongyi Liu, Jiaozuo (CN); Peiliang Ren, Jiaozuo (CN); Mingguo Hua, Jiaozuo (CN); Chenhui Luo, Jiaozuo (CN); Nan Li, Jiaozuo (CN); Xianjie Hao, Jiaozuo (CN); Duzhou Li, Jiaozuo (CN); Wei He, Jiaozuo (CN); Zhuang Li, Jiaozuo (CN); Jinhua Li, Jiaozuo (CN); Shibiao Sun, Jiaozuo (CN); Shilin Zhang, Jiaozuo (CN); Zhen Li, Jiaozuo (CN); Gongda Wang, Jiaozuo (CN); Weiyong Lu, Jiaozuo (CN)

(73) Assignee: Henan Polytechnic University, Jiaozuo (CN)

( * ) Notice: Subject to any disclaimer, the term of this patent is extended or adjusted under 35 U.S.C. 154(b) by 0 days.

(21) Appl. No.: 18/807,804

(22) Filed: Aug. 16, 2024

(65) Prior Publication Data

US 2025/0067180 A1    Feb. 27, 2025

(30) Foreign Application Priority Data

Aug. 23, 2023    (CN) .......................... 202311061913.X

(51) Int. Cl.
*E21F 17/18*    (2006.01)
*E21F 1/04*    (2006.01)
(Continued)

(52) U.S. Cl.
CPC .............. *E21F 17/185* (2013.01); *E21F 1/04* (2013.01); *E21F 1/08* (2013.01); *G01N 33/0031* (2013.01); *G08B 21/12* (2013.01); *E21F 1/003* (2013.01)

(58) Field of Classification Search
CPC ... E21F 17/185; E21F 1/04; E21F 1/08; E21F 1/003; G01N 33/0031; G08B 21/12
See application file for complete search history.

(56) References Cited

U.S. PATENT DOCUMENTS

| | | | |
|---|---|---|---|
| 6,851,757 B2 * | 2/2005 | Fourie | E21C 41/16 299/11 |
| 8,297,351 B2 * | 10/2012 | Yoshiuchi | G01N 27/4146 166/250.01 |

(Continued)

FOREIGN PATENT DOCUMENTS

| CN | 101532397 A | 9/2009 |
|---|---|---|
| CN | 102608286 A | 7/2012 |

(Continued)

*Primary Examiner* — Mohamed Barakat

(57) ABSTRACT

A coal and gas outburst monitoring device includes the insertion and anchoring assembly, and the pump drainage and monitoring mechanism; the insertion and anchoring assembly is vertically inserted and distributed on the sidewall of surrounding rock of coal mine roadway, and the insertion and anchoring assembly can monitor the stress change data in the sidewall of surrounding rock in real time; the pump drainage and monitoring mechanism is erected within the coal mine roadway, and the pump drainage and monitoring mechanism can cooperate with the insertion and anchoring assembly to perform the gas pump drainage monitoring for the sidewall of surrounding rock of goaf, and to obtain the gas seepage monitoring data in the surface layer and the inner layer of sidewall of surrounding rock. Thus, comparing with the database mechanism, the accurate and advanced predictions for the gas outburst can be made.

8 Claims, 6 Drawing Sheets

(51) Int. Cl.
*E21F 1/08* (2006.01)
*G01N 33/00* (2006.01)
*G08B 21/12* (2006.01)
*E21F 1/00* (2006.01)

(56) References Cited

U.S. PATENT DOCUMENTS

| | | | |
|---|---|---|---|
| 10,677,046 B2* | 6/2020 | Mohaghegh | E21B 47/10 |
| 11,704,449 B1* | 7/2023 | Mao | G06T 17/05 |
| | | | 703/10 |
| 2012/0039668 A1 | 2/2012 | Park et al. | |
| 2017/0122822 A1* | 5/2017 | Wang | E21F 17/18 |
| 2017/0285211 A1* | 10/2017 | Monteiro | G01V 3/24 |
| 2020/0200004 A1 | 6/2020 | Wang et al. | |
| 2022/0316323 A1 | 10/2022 | Zhou et al. | |
| 2023/0175398 A1* | 6/2023 | Wang | E21F 1/00 |
| | | | 454/168 |

FOREIGN PATENT DOCUMENTS

| | | |
|---|---|---|
| CN | 102691522 A | 9/2012 |
| CN | 102926810 A | 2/2013 |
| CN | 202946197 U | 5/2013 |
| CN | 103147799 A | 6/2013 |
| CN | 103528951 A | 1/2014 |
| CN | 106555614 A | 4/2017 |
| CN | 106873029 A | 6/2017 |
| CN | 110130990 A | 8/2019 |
| CN | 113374525 A | 9/2021 |

* cited by examiner

COAL AND GAS OUTBURST MONITORING DEVICE

CROSS REFERENCE TO RELATED APPLICATIONS

This application claims foreign priority of Chinese Patent Application No. 202311061913.X, filed on Aug. 23, 2023 in the China National Intellectual Property Administration, the disclosures of all of which are hereby incorporated by reference.

TECHNICAL FIELD

The present disclosure relates to the technical field of coal mine disaster prediction, and in particular to a coal and gas outburst monitoring device.

BACKGROUND

Coal and gas outburst is a type of special gas emission phenomenon, which refers to the phenomenon where broken coal and gas are suddenly ejected in large quantities from the coal body into the mining space under pressure. At present, due to the insufficient understanding of gas outburst laws of coal and gas in different mining areas and mining process conditions, the coal and gas outburst accidents still occur from time to time. In existing technology, a plurality of sensors are commonly used for monitoring in the gas outburst monitoring, such as gas concentration sensors, temperature and humidity sensors, pressure sensors and the like. However, due to the fact that the above-mentioned devices can only provide the gas concentration changes in the gas monitoring, but cannot make the accurate and advanced predictions for the gas outburst based on the underground environment; accordingly, there is a need to provide a coal and gas outburst monitoring device to solve the above-mentioned problems in the background.

SUMMARY

In order to achieve the above-mentioned object, the present disclosure provides the following technical solutions: a coal and gas outburst monitoring device, wherein, including: an insertion and anchoring assembly, and a pump drainage and monitoring mechanism; and the insertion and anchoring assembly is vertically inserted and distributed on a sidewall of a surrounding rock of a coal mine roadway; and the pump drainage and monitoring mechanism is erected within the coal mine roadway; and wherein, the pump drainage and monitoring mechanism includes a ground rail, a column frame, a connecting and guiding frame, and a docking assembly; and the ground rail is parallel laid on a roadway ground; and the column frame is slidably connected to the ground rail through a sliding seat, the column frame is vertically fixed above the sliding seat, and a position between the column frame is laterally connected with a fixing frame; and the connecting and guiding frame is vertically fixed on the column frame; and the docking assembly is slidably provided on the connecting and guiding frame, and the docking assembly is configured for performing an end sealing docking with the insertion and anchoring assembly; and the insertion and anchoring assembly includes a fixing anchor rod, an airflow hole, a drilling hole vacancy, and an insertion tube; and the fixing anchor rod is configured as a hollow rod frame structure, one end of the fixing anchor rod is provided with a joint sleeve in a sleeving mode, and one end of the joint sleeve is extended into the pump drainage and monitoring mechanism and is correspondingly communicated to the docking assembly in the pump drainage and monitoring mechanism; and the airflow hole is evenly distributed on the fixing anchor rod along a circumference; and the drilling hole vacancy is arranged and distributed on the fixing anchor rod, and the drilling hole vacancy is defined inside the sidewall of the surrounding rock of the coal mine roadway through a drilling machine; and the insertion tube is provided correspondingly to the drilling hole vacancy, and one end of the insertion tube is correspondingly communicated to the drilling hole vacancy, another end of the insertion tube is run through and located on an outer side wall of the surrounding rock of the coal mine roadway, and the insertion tube is defined with a through-hole; and the insertion tube is buried in a sidewall of the surrounding rock of the coal mine roadway from different directions, an end of the insertion tube is provided with an one-way valve, and the fixing anchor rod is distributed with a stress section; and an inner portion of the fixing anchor rod is slidably provided with a locating plug in a sealing mode, and the inner portion of the locating plug is coaxially provided with an inner tube in a penetrating mode, and the inner portion of the joint sleeve is provided with a cutting tube, which is communicated to the inner tube through a telescopic hose.

Beneficial Effects

The present disclosure is mainly based on the stress changes in the sidewall of surrounding rock of coal mine roadway and the gas permeation concentration changes in the surface layer and inner layer of sidewall of surrounding rock to monitor. Thus, comparing with the database mechanism, the accurate and advanced predictions for the gas outburst can be made.

LABLES AND DESCRIPTIONS

1—pump drainage and monitoring mechanism; 11—ground rail; 12—column frame; 13—fixing frame; 14—connecting and guiding frame; 15—sliding seat; 2—insertion and anchoring assembly; 21—fixing anchor rod; 22—joint sleeve; 23—drilling hole vacancy; 24—insertion tube; 25—stress section; 26—locating plug; 27—inner tube; 28—airflow hole; 29—through-hole; 3—docking assembly; 31—sealing cylinder seat; 32—fixing and connecting tube; 33—screw; 34—telescopic tube; 35—flow tube; 36—bearing rod; 37—sealing rubber; 4—cavity surround component; 41—sealing ring plug; 42—shaft ring frame; 43—clamping component; 44—abutting ring; 45—pneumatic tube; 5—one-way valve; 6—cutting tube; 7—telescopic hose.

DETAILED DESCRIPTION OF THE EMBODIMENTS

Figure 1:
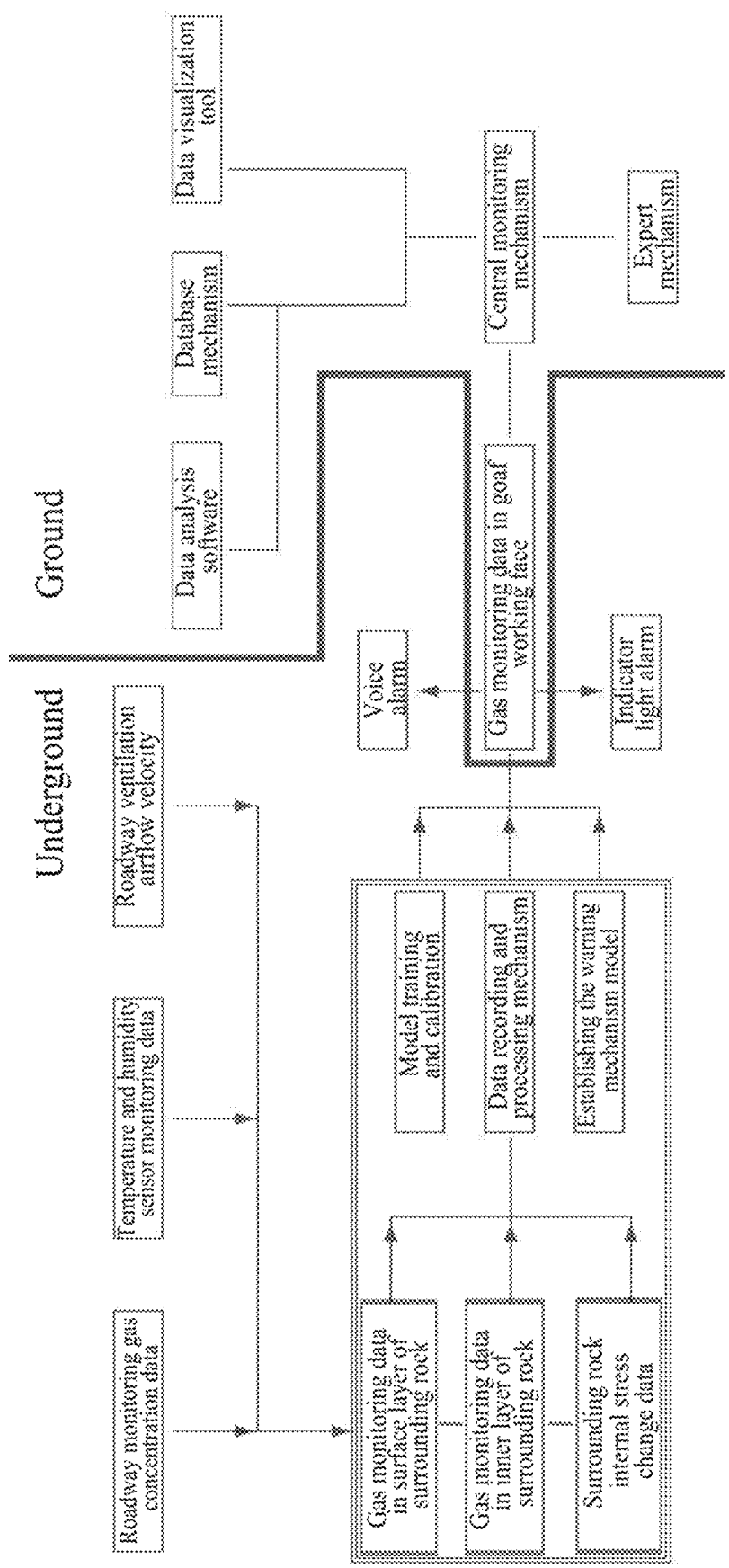
FIG. 1 is a workflow schematic diagram according to an embodiment of the present disclosure.
Figure 2:
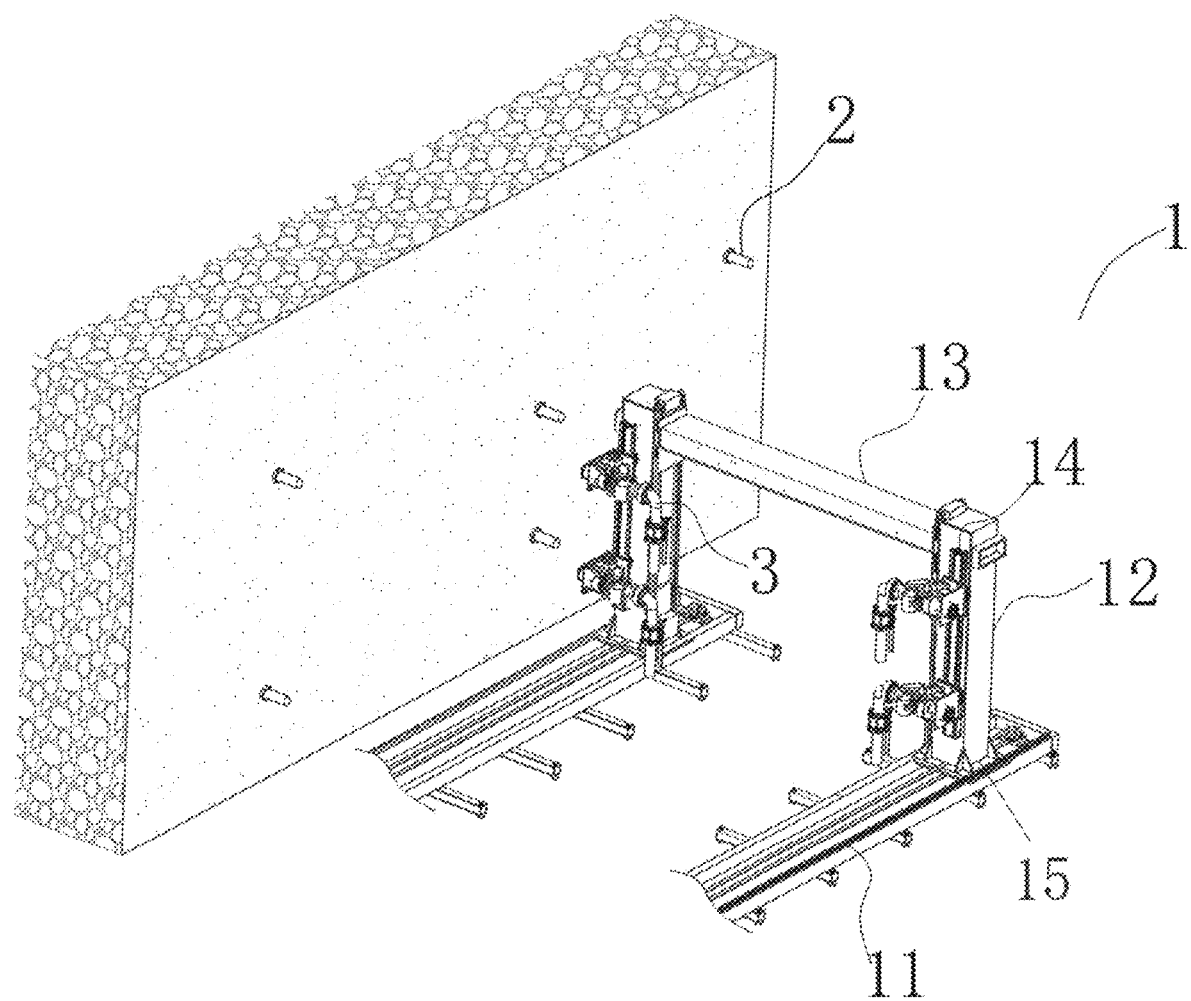
FIG. 2 is a structure schematic diagram of a pump drainage and a monitoring mechanism according to an embodiment of the present disclosure.
Figure 3:
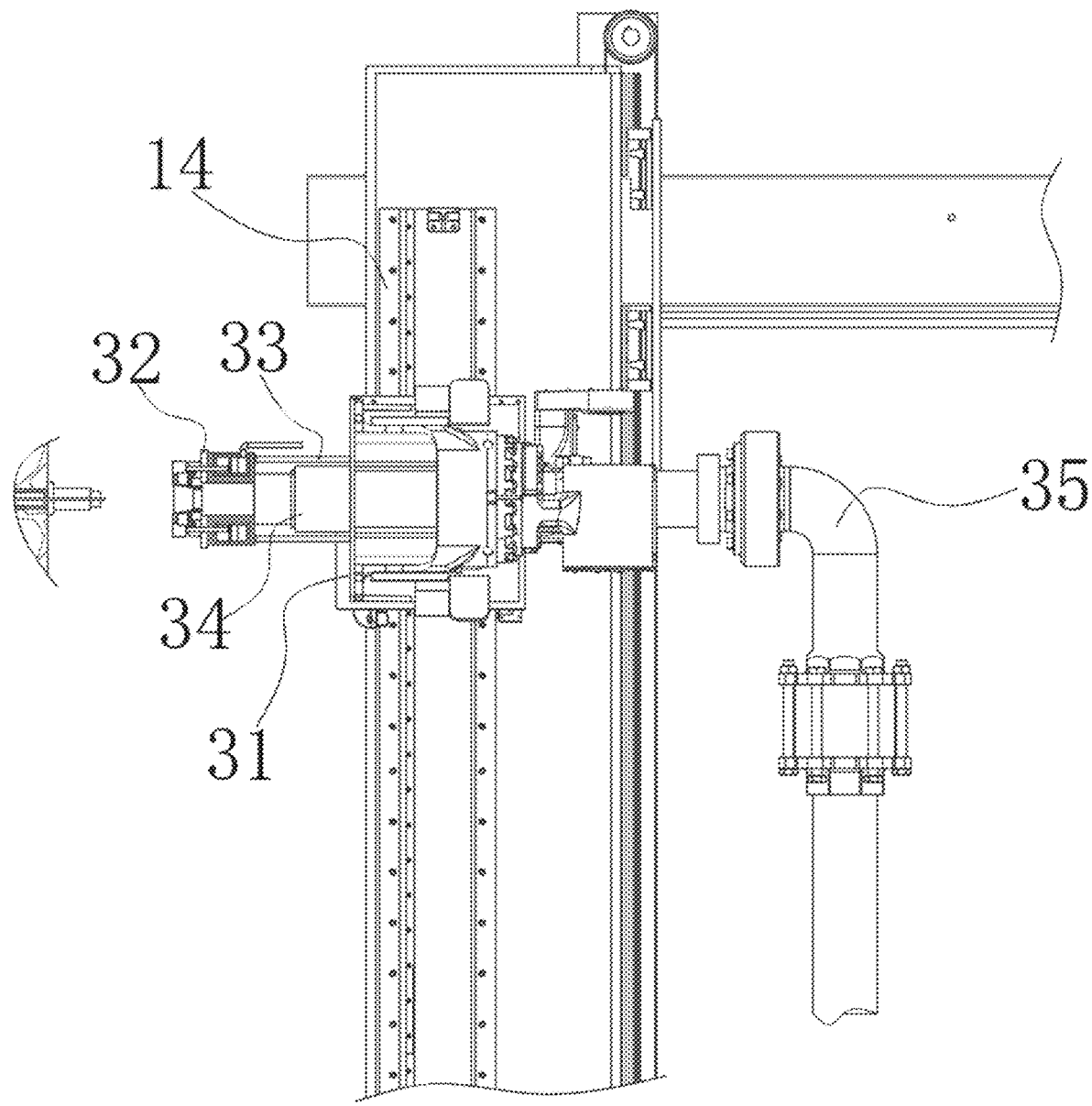
FIG. 3 is a structure schematic diagram of a docking assembly according to an embodiment of the present disclosure.
Figure 4:
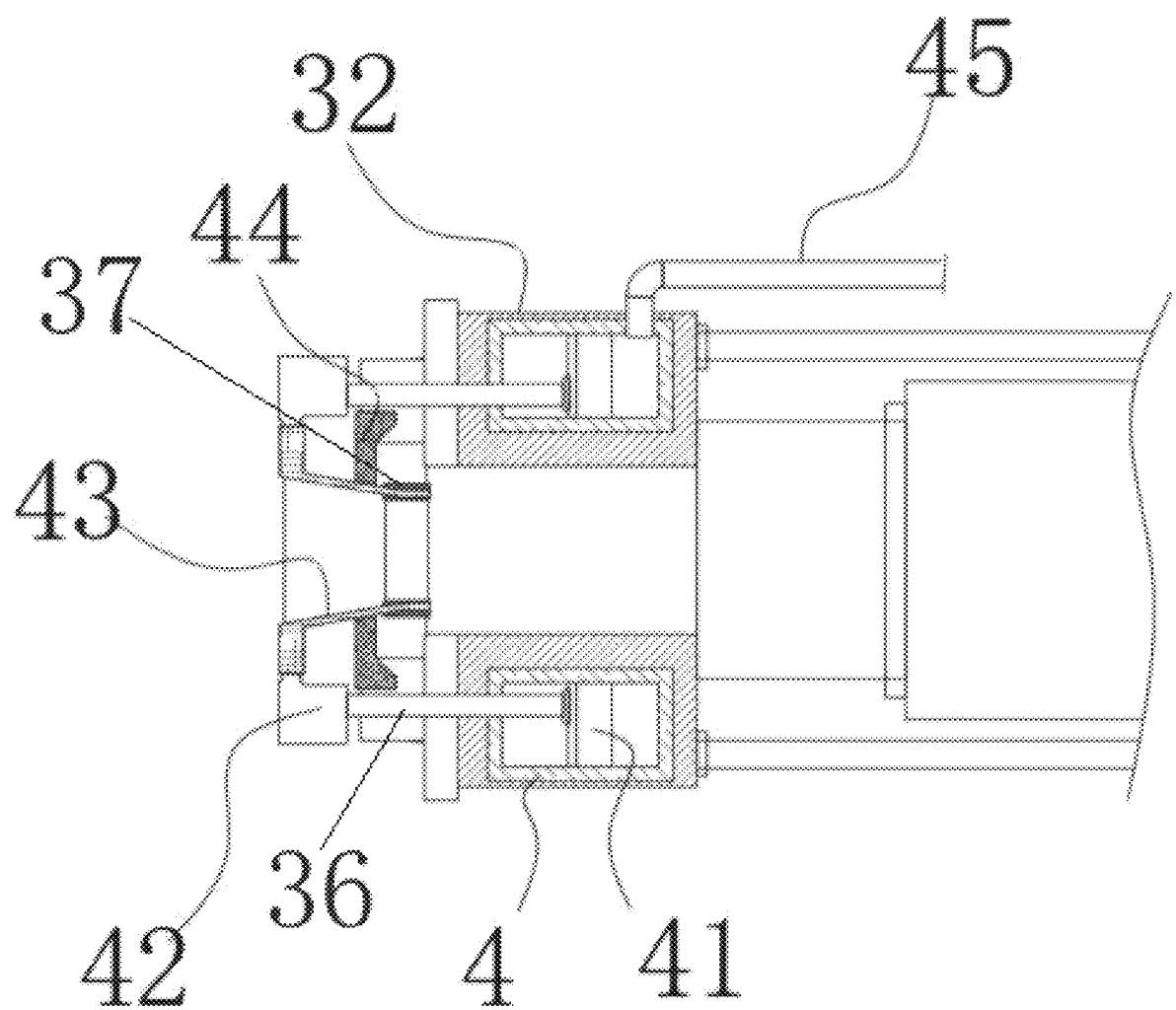
FIG. 4 is a structure schematic diagram of a cavity surround component according to an embodiment of the present disclosure.
Figure 5:
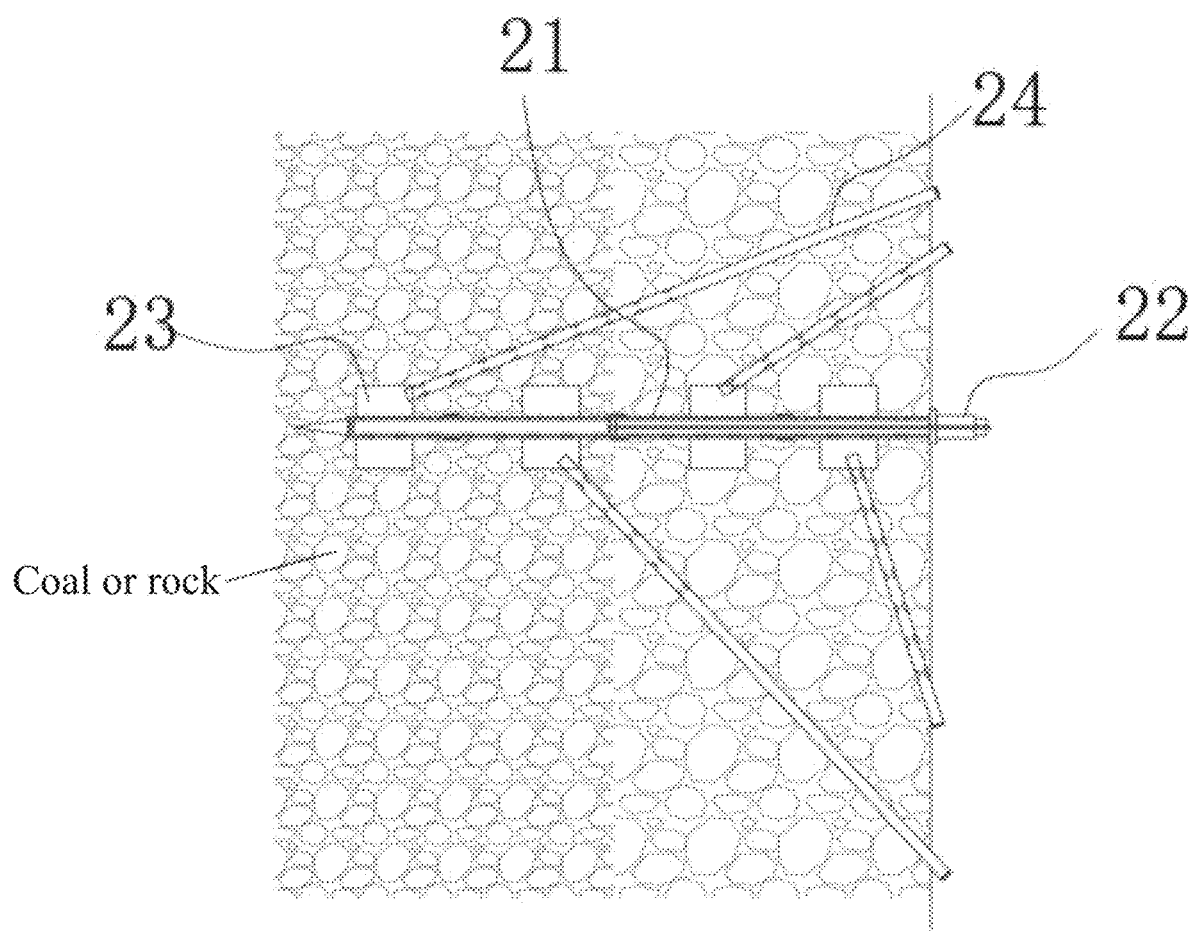
FIG. 5 is a structure schematic diagram of an insertion and anchoring assembly according to an embodiment of the present disclosure.
Figure 6:
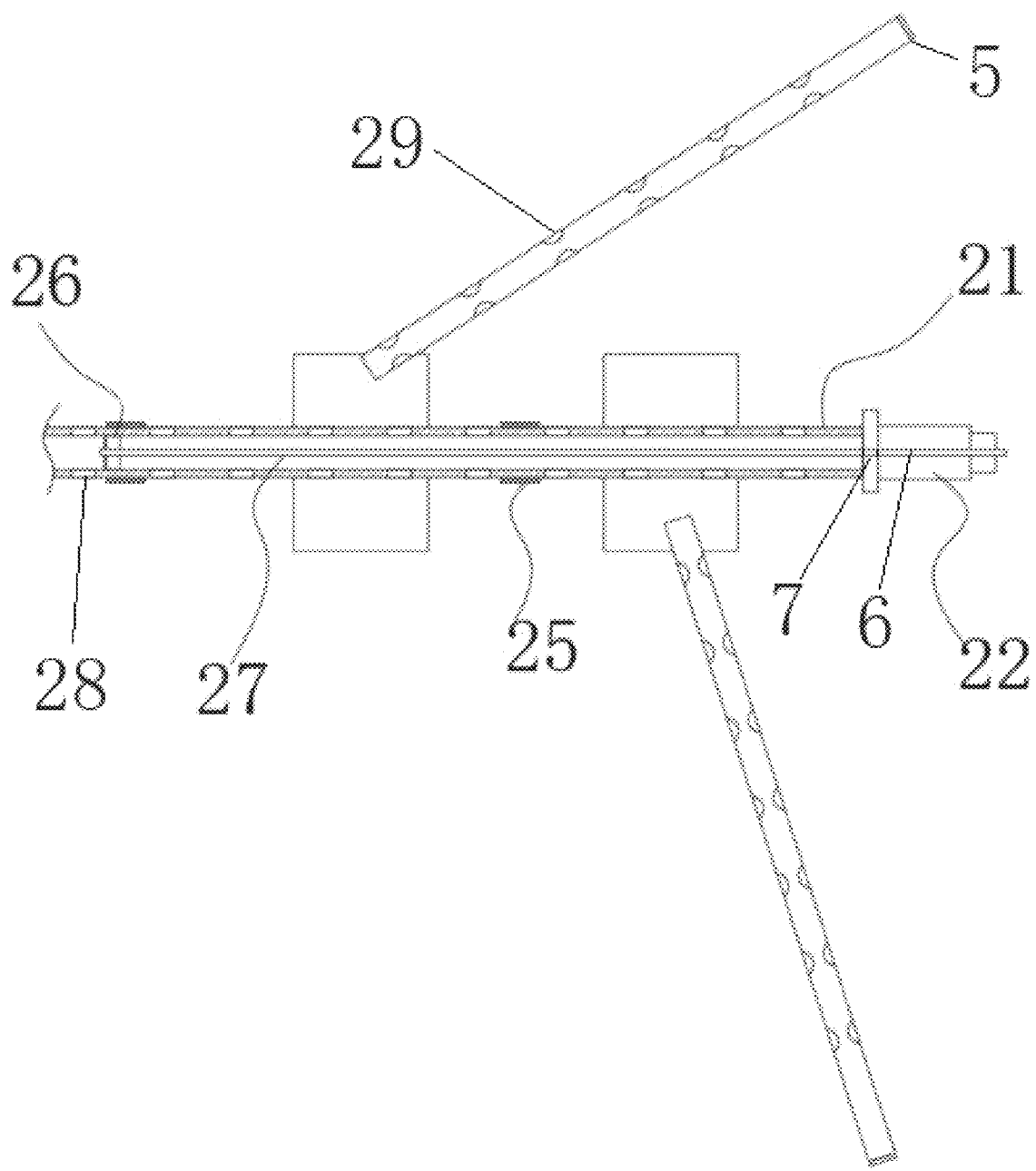
FIG. 6 is a structure schematic diagram relates to locating according to an embodiment of the present disclosure.

As shown in FIG. 1, in the embodiment of the present disclosure, a coal and gas outburst monitoring device includes: the gas concentration sensors, the temperature and humidity sensors, the insertion and anchoring assembly 2, the pump drainage and monitoring mechanism 1, the voice alarm, the alarm light, and the camera device.

The gas concentration sensors are evenly arranged within the coal mine roadway, and are used for monitoring the gas concentration at region ranges in real time.

In this embodiment, the gas concentration in the mine main return airway or one wing return airway is 0.5% to 0.6%, and the gas concentration in the airflow of the return airway of the mining area and the mining working face is 0.7% to 0.8%.

The temperature and humidity sensors are distributed within the coal mine roadway, wherein the wind direction sensors are also provided within the coal mine roadway.

The insertion and anchoring assembly 2 is vertically inserted and distributed on a sidewall of a surrounding rock of a coal mine roadway, and the insertion and anchoring assembly 2 can monitor the stress change data in the sidewall of the surrounding rock in real time.

In this embodiment, the stress change of the sidewall of the surrounding rock of the deep coal mine roadway is 20 MPa to 40 MPa.

The pump drainage and monitoring mechanism 1 is erected within the coal mine roadway, and the pump drainage and monitoring mechanism 1 can cooperate with the insertion and anchoring assembly 2 to perform the gas pump drainage monitoring for the sidewall of the surrounding rock of the goaf, and to obtain the gas seepage monitoring data in the surface layer and the inner layer of the sidewall of the surrounding rock, and a warning mechanism model can be established based on the monitoring data; that is to say, the relationship between gas concentration and gas outburst probability in the sidewall of the surrounding rock may manifest in the following situations: (1) the gas concentration in the sidewall of the surrounding rock is increased, and the gas outburst probability is increased, if the gas concentration in the sidewall of the surrounding rock of the coal mine is high, it may indicate the presence of a large amount of gas storage in the sidewall or a path for gas infiltration; the sidewall of the surrounding rock with high gas concentration may increase the gas outburst probability, and the gas may suddenly emerge under certain conditions; (2) the gas concentration in the sidewall of the surrounding rock is relatively low, and the gas outburst probability is relatively low, the sidewall of the surrounding rock with low gas concentration may indicate less gas storage or limited gas permeability, in this case, the gas outburst probability may be relatively low; (3) the gas concentration between the surface layer and the inner layer of the sidewall of the surrounding rock is different, if there is a significant difference in the gas concentration between the surface layer and the inner layer of the sidewall of the surrounding rock, it may affect the occurrence of the gas outburst, if the gas concentration in the inner layer is high and the gas concentration in the surface layer is low, this may lead to sudden gas outburst under certain conditions, thereby increasing the gas outburst probability.

In this embodiment, the gas concentration data in the inner layer of the sidewall of the surrounding rock is 40% to 96%, and the gas concentration data in the surface layer of the sidewall of the surrounding rock is greater than 0.6%.

The voice alarm and the alarm light is correspondingly distributed at the wellhead and the working face, which is used to issue the strong warning alarm.

The camera device has the data storage, the real-time display, the alarm triggering, and the data analysis. The camera device is combined with the data analysis software, the database mechanism (the database is used to store a large amount of monitoring data for querying, analysis and comparison at any time), and the data visualization tools to analyze the gas concentration monitoring data in the coal mine roadway. These tools are used to visualize the monitoring data in the form of charts, graphics, maps and the like, which make the data analysis results easier to understand and identify, so as to identify the potential outburst risks. At the same time, the camera device is also externally provided with an expert mechanism, which uses the expert mechanism technology to integrate the knowledge and experience of the mine safety experts into the data analysis, so as to provide more accurate outburst risk assessment.

In this embodiment, the camera device is combined with the NewSQL database mechanism, and the Matlab is used for data prediction analysis and visualization operations.

In this embodiment, the pump drainage and monitoring mechanism 1 includes a ground rail 11, a column frame 12, a connecting and guiding frame 14, and a docking assembly 3; and the ground rail 11 is parallel laid on a roadway ground; and the column frame 12 is slidably connected to the ground rail 11 through a sliding seat 15, the column frame 12 is vertically fixed above the sliding seat 15, and a position between the column frame 12 is laterally connected with a fixing frame 13; and the connecting and guiding frame 14 is vertically fixed on the column frame 12; and the docking assembly 3 is slidably provided on the connecting and guiding frame 14, and the docking assembly 3 is configured for performing an end sealing docking with the insertion and anchoring assembly 2.

As a preferred embodiment, the docking assembly 3 includes a sealing cylinder seat 31, a screw 33, and a telescopic tube 34; and the sealing cylinder seat 31 is slidably provided on the connecting and guiding frame 14, and one side of the sealing cylinder seat 31 is provided with a fixing and connecting tube 32; and the screw 33 is horizontally symmetrically fixed on a upper side and a lower side of the fixing and connecting tube 32, one end of the screw 33 is slidably extended into the sealing cylinder seat 31, and the telescopic tube 34 is connected between the sealing cylinder seat 31 and the fixing and connecting tube 32; and the telescopic tube 34 is horizontally communicated between the sealing cylinder seat 31 and the fixing and connecting tube 32, and one side of the sealing cylinder seat 31 is connected with a flow tube 35. Wherein, at the coal mine roadway of the goaf, the docking assembly 3 can intermittently monitor the gas concentration one by one in the sidewall of the surrounding rock at the insertion and anchoring assembly area under the displacement driving. Wherein, the docking assembly 3 is docked outside the insertion and anchoring assembly 2, and is used for performing the gas pump drainage to the sidewall of the surrounding rock through the flow tube 35, while the concentration detection is performed, the data summary is generated, and it is analyzed and compared through the database mechanism in the camera device, so as to make the accurate and advanced predictions for the coal and gas outburst.

In this embodiment, the inner portion of the fixing and connecting tube 32 is coaxially provided with a cavity surround component 4, the inner portion of the cavity surround component 4 is slidably provided with a sealing ring plug 41, one side of the fixing and connecting tube 32 is provided with a shaft ring frame 42, the shaft ring frame 42 is connected to the sealing ring plug 41 through a bearing rod 36, the shaft ring frame 42 is distributed with a clamping component 43 in an inner circumference, a cross-section of the clamping component 43 is a L-shaped structure, the shaft ring frame 42 is provided with an abutting ring 44, one side wall of the clamping component 43 is abutted against and in contact with the abutting ring 44, the end of the clamping component 43 is provided with a sealing rubber 37, a contacting face between the clamping component 43 and the abutting ring 44 is configured as an inclining structure, and the cavity surround component 4 is externally connected with a pneumatic tube 45, which drive the sealing ring plug 41 to move laterally, so as to connect and fix the end of the insertion and anchoring assembly 2 from the side panel by the clamping component 43.

In this embodiment, a gas supply tube (not shown in the figure) is also provided on the sealing cylinder seat 31. Wherein, after the gas concentration exceeds the standard and the ventilation treatment is performed, the pump drainage and monitoring mechanism 1 can supply the gas and increase the pressure to the sidewall of the surrounding rock through the gas supply tube on the sealing cylinder seat 31 in conjunction with the insertion and anchoring assembly 2 one by one, which can bring the following situations.

(1) Controlling the gas concentration: it can change the gas composition inside the roadway, thereby reducing the concentration of gas. This helps to further reduce the risk of gas explosion.

(2) Preventing the gas infiltration: it can fill the roadway space, reduce the possibility of the gas infiltration, and thus reduce the transmission of the gas between the coal seams and the rock walls.

(3) Reducing the fire risk: it can dilute the gas concentration, reduce the possibility of fire and explosion, and make the gas in the roadway safer.

(4) Auxiliary ventilation: the injected gas can assist the ventilation mechanism, help the fresh air to circulate better and reduce the dead corners and the air accumulation.

In this embodiment, the insertion and anchoring assembly 2 includes a fixing anchor rod 21, an airflow hole 28, a drilling hole vacancy 23, and an insertion tube 24; and the fixing anchor rod 21 is configured as a hollow rod frame structure, one end of the fixing anchor rod 21 is provided with a joint sleeve 22 in a sleeving mode, and one end of the joint sleeve 22 is extended into the pump drainage and monitoring mechanism 1 and is correspondingly communicated to the docking assembly 3 in the pump drainage and monitoring mechanism 1; and the airflow hole 28 is evenly distributed on the fixing anchor rod 21 along a circumference; the drilling hole vacancy 23 is arranged and distributed on the fixing anchor rod 21, and the drilling hole vacancy 23 is defined inside the sidewall of the surrounding rock of the coal mine roadway through a drilling machine; and the insertion tube 24 is provided correspondingly to the drilling hole vacancy 23, and one end of the insertion tube 24 is correspondingly communicated to the drilling hole vacancy 23, another end of the insertion tube 24 is run through and located on an outer side wall of the surrounding rock of the coal mine roadway, and the insertion tube 24 is defined with a through-hole 29; wherein, after docking with the fixing anchor rod 21, the pump drainage and monitoring mechanism 1 can pump the gas through the airflow hole 28 on the fixing anchor rod 21 under negative pressure, while the insertion tube 24 on the drilling hole vacancy 23 can pump the gas through the through-hole 29, thus achieving the pump drainage and the monitoring of the gas seepage concentration in the sidewall of the surrounding rock.

As a preferred embodiment, the insertion tube 24 is buried in a sidewall of the surrounding rock of the coal mine roadway from different directions, an end of the insertion tube 24 is provided with an one-way valve 5, which can be in a closed state during the gas pumping of the insertion tube 24 to prevent the gas inside the roadway from entering the insertion tube 24. During high-pressure gas injection, the one-way valve 5 can be opened to achieve the gas flow ventilation and discharge in the sidewall of the surrounding rock, the fixing anchor rod 21 is distributed with a stress section 25, which can monitor the internal stress changes of the sidewall of the surrounding rock in real time.

Assuming the gas concentration in the surface of the surrounding rock is $C\_s$, the gas concentration in the inner layer is $C\_i$, the gas concentration inside the roadway is $C\_g$, the ventilation efficiency is V, and the gas permeability coefficient is K.

The simplified mathematical relationship is as following.

$C\_g=(C\_s+C\_i*K)*V$, which enables the accurate and advanced predictions based on the gas seepage concentration in the sidewall of the surrounding rock.

In this embodiment, an inner portion of the fixing anchor rod 21 is slidably provided with a locating plug 26 in a sealing mode, and the inner portion of the locating plug 26 is coaxially provided with an inner tube 27 in a penetrating mode, and the inner portion of the joint sleeve 22 is provided with a cutting tube 6, which is communicated to the inner tube 27 through a telescopic hose 7. Especially, in the axial displacement adjustment of the locating plug 26, the fixing anchor rod 21 can be divided into two compartments with the same or different sizes, the joint sleeve 22 transports and performs the pump drainage to the gas flow to the compartment close to the position, while the inner tube 27 transports and performs the pump drainage to the gas flow to another compartment, thus achieving the monitoring of gas seepage concentration in the inner layer and the surface layer of the sidewall of the surrounding rock. It should be noted that the through-hole 29 connected on the insertion tube 24 in the inner layer is distributed on one side (i.e. it is only distributed on the side closer to the center, without defining the through-hole 29 near the surface layer), so as to avoid the gas in the surface layer entering and affecting the monitoring accuracy.

Specifically, according to the distribution conditions of coal mine in the surrounding rock of the coal mine roadway, the fixing anchor rod 21 is inserted correspondingly, and the docking assembly 3 in the pump drainage and monitoring mechanism 1 is sealed and connected with the fixing anchor rod 21 one by one in a fixed time period, and the concentration of gas pumping is monitored, so as to obtain the gas seepage flow in the surface layer and the inner layer of the sidewall of the surrounding rock of the coal mine roadway, and a warning mechanism model can be established, and it is analyzed and compared through the database mechanism in the camera device, so as to make accurate and advanced predictions for the coal and gas outburst.

What is claimed is:

1. A coal and gas outburst monitoring device, comprising:
gas concentration sensors evenly arranged within a coal mine roadway, and used for monitoring the gas concentration at region ranges in real time;
temperature and humidity sensors distributed within the coal mine roadway; wherein, wind direction sensors are provided within the coal mine roadway;
an insertion and anchoring assembly, vertically inserted and distributed on a sidewall of a surrounding rock of the coal mine roadway; wherein the insertion and anchoring assembly is configured for monitoring stress change data in the sidewall of the surrounding rock in real time;
a pump drainage and monitoring mechanism, erected within the coal mine roadway;
wherein the pump drainage and monitoring mechanism is configured for cooperating with the insertion and anchoring assembly to perform a gas pump drainage monitoring for the sidewall of the surrounding rock of a goaf, to obtain gas seepage monitoring data in a surface layer and an inner layer of the sidewall of the surrounding rock;
a voice alarm and the alarm light, correspondingly distributed at a wellhead and a working face, which is used to issue a warning alarm;
a central monitor system, having data storage, a real-time display, an alarm triggering, and data analysis; wherein the central monitor system is combined with a data analysis software, a database mechanism, and data visualization tools to analyze gas concentration monitoring data in the coal mine roadway.

2. The coal and gas outburst monitoring device according to claim 1, wherein the pump drainage and monitoring mechanism comprises a ground rail, a column frame, a connecting and guiding frame, and a docking assembly;
the ground rail is parallel laid on a roadway ground;
the column frame is slidably connected to the ground rail through a sliding seat, the column frame is vertically fixed above the sliding seat, and a position between the column frame is laterally connected with a fixing frame;
the connecting and guiding frame is vertically fixed on the column frame; and
the docking assembly is slidably provided on the connecting and guiding frame, and the docking assembly is configured for performing an end sealing docking with the insertion and anchoring assembly.

3. The coal and gas outburst monitoring device according to claim 2, wherein the docking assembly comprises a sealing cylinder seat, a screw, and a telescopic tube;
the sealing cylinder seat is slidably provided on the connecting and guiding frame, and one side of the sealing cylinder seat is provided with a fixing and connecting tube;
the screw is horizontally symmetrically fixed on a upper side and a lower side of the fixing and connecting tube, one end of the screw is slidably extended into the sealing cylinder seat, and the telescopic tube is connected between the sealing cylinder seat and the fixing and connecting tube; and
the telescopic tube is horizontally communicated between the sealing cylinder seat and the fixing and connecting tube, and one side of the sealing cylinder seat is connected with a flow tube.

4. The coal and gas outburst monitoring device according to claim 3, wherein an inner portion of the fixing and connecting tube is coaxially provided with a cavity surround component;
the inner portion of the cavity surround component is slidably provided with a sealing ring plug;
one side of the fixing and connecting tube is provided with a shaft ring frame;
the shaft ring frame is connected to the sealing ring plug through a bearing rod;
the shaft ring frame is distributed with a clamping component in an inner circumference;
a cross-section of the clamping component is a L-shaped structure;
the shaft ring frame is provided with an abutting ring;
one side wall of the clamping component is abutted against and in contact with the abutting ring;
the end of the clamping component is provided with a sealing rubber;
a contacting face between the clamping component and the abutting ring is configured as an inclining structure; and
the cavity surround component is externally connected with a pneumatic tube.

5. The coal and gas outburst monitoring device according to claim 3, wherein a gas supply tube is provided on the sealing cylinder seat.

6. The coal and gas outburst monitoring device according to claim 1, wherein the insertion and anchoring assembly comprises
a fixing anchor rod; wherein the fixing anchor rod is configured as a hollow rod frame structure; one end of the fixing anchor rod is provided with a joint sleeve in a sleeving mode; and one end of the joint sleeve is extended into the pump drainage and monitoring mechanism and is correspondingly communicated to the docking assembly in the pump drainage and monitoring mechanism;
an airflow hole, distributed on the fixing anchor rod;
a drilling hole vacancy, arranged and distributed on the fixing anchor rod; wherein the drilling hole vacancy is defined inside the sidewall of the surrounding rock of the coal mine roadway through a drilling machine; and
an insertion tube, provided correspondingly to the drilling hole vacancy; wherein one end of the insertion tube is correspondingly communicated to the drilling hole vacancy, another end of the insertion tube is run through and located on an outer side wall of the surrounding rock of the coal mine roadway; the insertion tube is defined with a through-hole.

7. The coal and gas outburst monitoring device according to claim 6, wherein the insertion tube is buried in the sidewall of the surrounding rock of the coal mine roadway from different directions; an end of the insertion tube is provided with an one-way valve; the fixing anchor rod 21 is distributed with a stress section.

8. The coal and gas outburst monitoring device according to claim 6, wherein an inner portion of the fixing anchor rod is slidably provided with a locating plug in a sealing mode, and the inner portion of the locating plug is coaxially provided with an inner tube in a penetrating mode, and the inner portion of the joint sleeve is provided with a cutting tube, which is communicated to the inner tube through a telescopic hose.

* * * * *